United States Patent [19]

Nagano et al.

[11] Patent Number: 5,030,761
[45] Date of Patent: Jul. 9, 1991

[54] ALKOXY-NITROBENZENE AND ALKOXY-AMINOBENZENE COMPOUNDS USEFUL IN THE PRODUCTION OF TETRAHYDROPHTALIMIDES

[75] Inventors: Eiki Nagano, Hyogo; Shunich Hashimoto, Osaka; Ryo Yoshida, Hyogo; Hiromichi Oshio; Katsuzo Kamoshita, both of Osaka, all of Japan

[73] Assignee: Sumitomo Chemical Company, Limited, Osaka, Japan

[21] Appl. No.: 553,391

[22] Filed: Nov. 21, 1983

Related U.S. Application Data

[62] Division of Ser. No. 360,998, Mar. 23, 1982, Pat. No. 4,431,822.

[30] Foreign Application Priority Data

Mar. 30, 1981 [JP] Japan .................................. 56-47816
Dec. 28, 1981 [JP] Japan ................................ 56-211414

[51] Int. Cl.$^5$ .................... C07C 211/00; C07C 43/20; C07C 205/06; C07C 205/07
[52] U.S. Cl. .................................. 564/442; 564/441; 564/443; 564/417; 564/418; 568/588; 71/95
[58] Field of Search ................. 564/441, 442; 568/588

[56] References Cited

U.S. PATENT DOCUMENTS 4,006,185  2/1977  Tobin et al. ........................ 564/442

FOREIGN PATENT DOCUMENTS 0068822  1/1983  European Pat. Off. ............ 564/442
2018248 11/1970  Fed. Rep. of Germany ...... 568/588
2748554  5/1978  Fed. Rep. of Germany .

Primary Examiner—Elizabeth C. Weimar
Assistant Examiner—Gail Peulos
Attorney, Agent, or Firm—Birch, Stewart, Kolasch & Birch

[57] ABSTRACT

A compound of the formula:

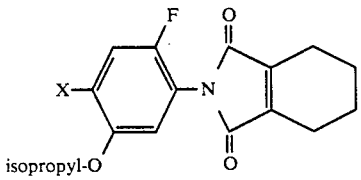

wherein X is a chlorine atom or a bromine atom, which is useful as a herbicide.

6 Claims, No Drawings

ALKOXY-NITROBENZENE AND ALKOXY-AMINOBENZENE COMPOUNDS USEFUL IN THE PRODUCTION OF TETRAHYDROPHTALIMIDES

This application is a divisional of copending application Ser. No. 360,998 filed on Mar. 23, 1982.

The present invention relates to N-(2-fluoro-4-halo-5-substituted phenyl)-3,4,5,6-tetrahydrophthalimide derivatives (hereinafter referred to as "tetrahydrophthalimide(s)"), and their production and use.

The said tetrahydrophthalimides are representable by the formula:

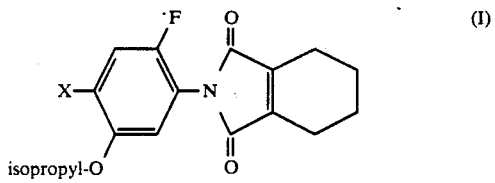

wherein X is a chlorine atom or a bromine atom.

It is known that certain kinds of N-phenyltetrahydrophthalimides are effective as herbicides. For instance, the herbicidal use of 2-fluoro-4-chlorophenyltetrahydrophthalimide, 2,4-dichloro-5-isopropoxyphenyltetrahydrophthalimide, etc. is disclosed in U.S. Pat. No. 4,032,326, U.K. Patent Publication No. 2046754A, etc. However, their herbicidal effect is still not always satisfactory.

It has now been found that the tetrahydrophthalimides (I) show a strong herbicidal activity against a wide variety of weeds including Gramineae weeds, Cyperaceae weeds and broad-leaved weeds at small doses and do not produce any material phytotoxicity on various agricultural crops. Examples of Gramineae weeds against which the tetrahydrophthalimides (I) show a herbicidal activity are barnyardgrass (*Echinochloa crus-galli*), green foxtail (*Setaria viridis*), large crabgrass (*Digitaria sanguinalis*), Johnsongrass (*Sorghum halepense*), wild oat (*Avena fatua*), water foxtail (*Alopecurus geniculatus*), goosegrass (*Eleusine indica*), annual bluegrass (*Poa annua*), bermudagrass (*Cynodon dactylon*), quackgrass (*Agropyron repens*), etc. Examples of Cyperaceae weeds are nutsedge sp. (*Cyperus* sp.), purple nutsedge (*Cyperus rotundus*), hardstem bulrush (*Scirpus juncoides*), nutsedge (*Cyperus serotinus*), water chestnut (*Eleocharis kuroguwai*), slender spikerush (*Eleocharis acicularis*), etc. Examples of broad-leaved weeds are tall morningglory (*Ipomoea purpurea*), velvetleaf (*Abutilon theophrasti*), sicklepod (*Cassia obtusifolia*), wild sunflower (*Helianthus annus*), cocklebur (*Xanthium pennsylvanicum*), wild mustard (*Brassica kaber*), common chickweed (*Stellaria media*), common purslane (*Portulaca oleracea*), jimsonweed (Datura stramonium), hempsesbania (*Sesbania exaltata*), sun spurge (*Euphorbia helioscopia*), prickly sida (*Sida spinosa*), common ragweed (*Ambrosia artemisifolia*), smartweed sp. (*Polygonum* sp.), redroot pigweed (*Amaranthus retroflexus*), bedstraw (*Galium aparine*), pineappleweed (*Matricaria* spp.), birdseye speedwell (*Veronica persica*), wild buckwheat (*Polygonum convolvulus*), ladysthumb (*Polygonum persicaria*), beggarticks (*Bidens* spp.) common lambsquarters (*Chenopodium album*), black nightshade (*Solanum nigrum*), bindweed (*Calystegia japonica*), monochoria (*Monochoria vaginalis*), American waterwort (*Elatine americana*), false pimpernel (*Lindernia procumbens*), toothcup (*Rotala indica*), arrowhead (*Sagittaria pygmaea*), etc.

Accordingly, the tetrahydrophthalimides (I) can be used as herbicides applicable for field crops and vegetables as well as paddy rice. They are also useful as herbicides to be employed for orchard, lawn, pasture, tea garden, mulberry field, rubber plantation, forest, etc. applications.

The tetrahydrophthalimides (I) can be produced by various procedures, among which typical examples are shown below.

Procedure A

The tetrahydrophthalimide (I) is obtainable by reacting an aniline of the formula:

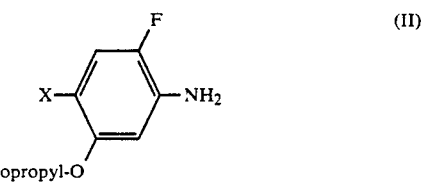

wherein X is as defined above with 3,4,5,6-tetrahydrophthalic anhydride, in the absence or presence of an inert solvent (e.g. benzene, toluene, xylene, 1,4-dioxane, acetic acid, propionic acid) while heating. The reaction is normally accomplished at a temperature of 70° to 200° C. for a period of 0.5 to 5 hours. The molar ratio of the aniline (II) and the tetrahydrophthalic anhydride is preferred to be from 1:1.0 to 1:1.1.

Procedure B

The tetrahydrophthalimide (I) is obtainable by reacting a hydroxyphenyltetrahydrophthalimide of the formula:

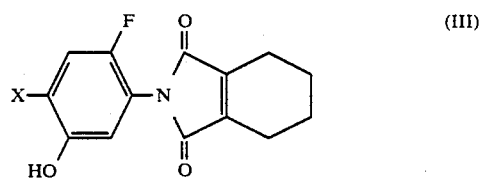

wherein X is as defined above with an isopropyl halide (e.g. isopropyl chloride, isopropyl bromide, isopropyl iodide), usually in an inert solvent (e.g. dimethylformamide, dimethyl sulfoxide) in the presence of a base such as an alkali metal carbonate (e.g. potassium carbonate), an alkali metal hydroxide (e.g. potassium hydroxide), an alkali metal hydride (e.g. sodium hydride) or an alkali metal alkoxide (e.g. sodium methoxide, sodium ethoxide). The most preferred base is an alkali metal carbonate. The reaction temperature is normally from 0° to 100° C., preferably from 40° to 90° C. The molar ratio of the hydroxyphenyltetrahydrophthalimide (III) and the halide is preferred to be from 1:1.0 to 1:1.1.

The thus produced tetrahydrophthalimide (I) may be, when desired, purified by a per se conventional procedure such as recrystallization or column chromatography.

The aniline (II) as the starting material in Procedure A and the hydroxyphenyltetrahydrophthalimide (III) as the starting material in Procedure B can be produced from a phenol of the formula:

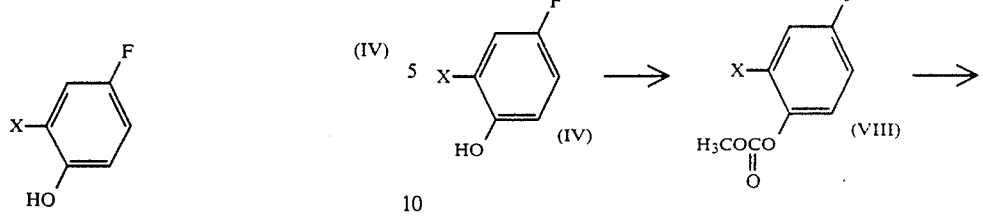

wherein X is as defined above according to the following scheme:

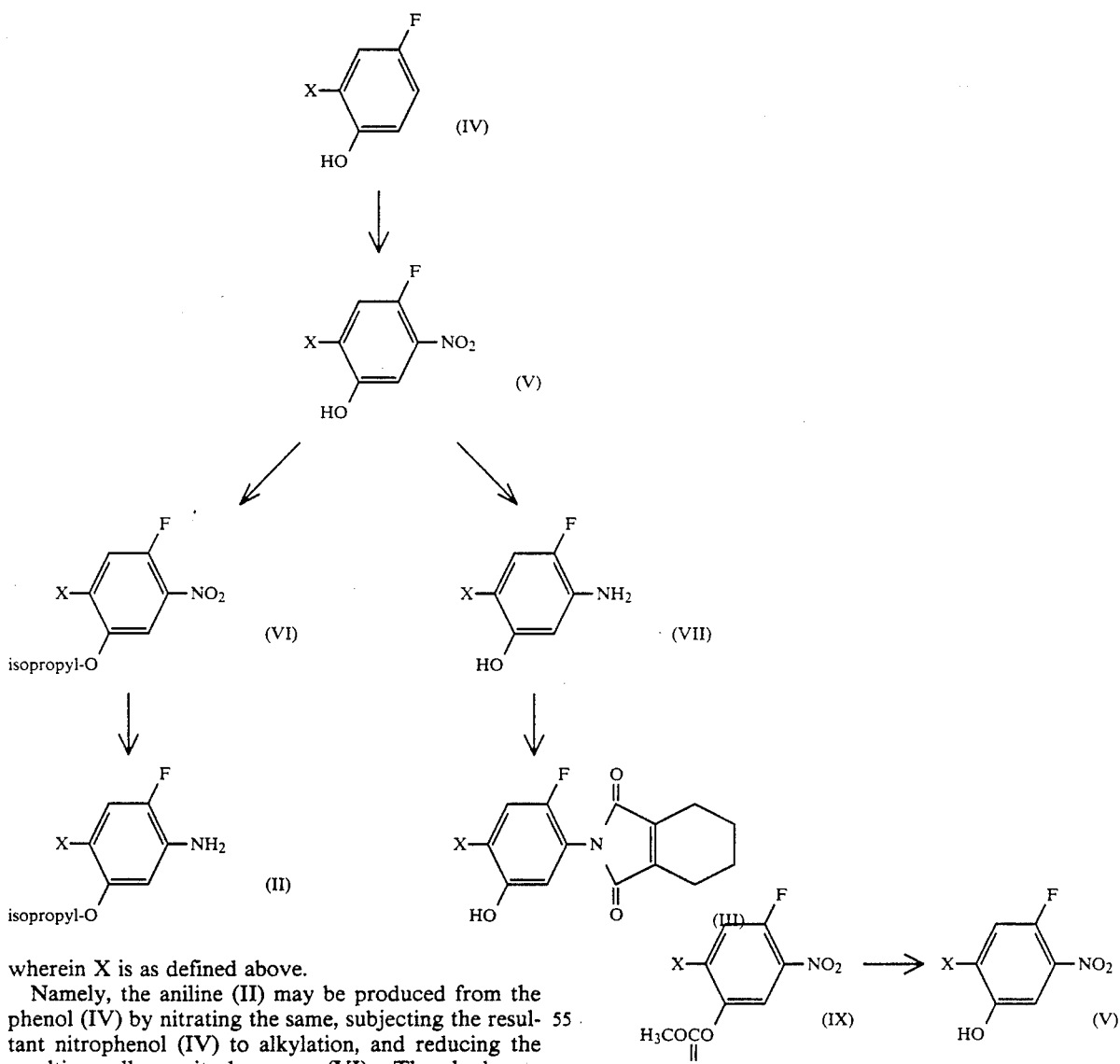

wherein X is as defined above.

Namely, the aniline (II) may be produced from the phenol (IV) by nitrating the same, subjecting the resultant nitrophenol (IV) to alkylation, and reducing the resulting alkoxy-nitrobenzene (VI). The hydroxyphenyltetrahydrophthalimide (III) can be manufactured from the phenol (IV) by nitrating the same, reducing the resultant nitrophenol (V) and reacting the resulting aminophenol (VII) with 3,4,5,6-tetrahydrophthalic anhydride.

Conversion of the phenol (IV) into the nitrophenol (V) may be accomplished by application of a per se conventional nitration procedure to the former. Usually, however, the indirect nitration which consists of the following three steps is favorable in achievement of the selective nitration at the desired position:

wherein X is as defined above. Thus, the phenol (IV) is converted into its alkali metal salt by treatment with an aqueous solution of an alkali metal hydroxide (e.g. sodium hydroxide, potassium hydroxide), and the resulting salt is reacted with an alkyl haloformate such as methyl chloroformate in water in a temperature of 0° to 10° C. The thus prepared carbonic ester (VIII) is nitrated with a mixture of conc. sulfuric acid and conc. nitric acid at room temperature. Then, the nitrobenzene (IV) thus obtained is hydrolyzed with an aqueous alkaline solution such as an aqueous sodium hydroxide solution at a temperature of 20° to 120° C. to give the nitrophenol (V).

The alkylation for conversion of the nitrophenol (V) into the alkoxy-nitrobenzene (VI) may be carried out by treatment of the former with an alkali metal carbonate (e.g. potassium carbonate), an alkali metal hydride (e.g. sodium hydride) or an alkali metal alkoxide (e.g. sodium methoxide) and reacting the resultant alkali metal salt with an isopropyl halide in a polar solvent (e.g. water, dimethylformamide, acetonitrile, acetone, dimethylsulfoxide), usually at a temperature of 10° to 200° C., preferably of 30° to 100° C. The use of a phase transfer catalyst such as tetrabutylammonium bromide is favorable for smooth accomplishment of the reaction.

Reduction of the alkoxy-nitrobenzene (VI) to the aniline (II) may be achieved by various procedures. For instance, there may be adopted a per se conventional reduction procedure for converting a nitro group into an amino group wherein a reducing agent such as sodium sulfide or iron powder or catalytic reduction is employed. One of the typical procedures comprises introduction of a 3 molar amount of hydrogen into a reaction system comprising one molar amount of the compound (VI) and a 1/10 to 1/100 molar amount of platinum dioxide at room temperature under atmospheric pressure. Another typical procedure comprises admixing an acetic acid solution containing one molar amount of the compound (VI) with a 5% acetic acid solution containing a 2 to 5 molar amount of iron powder such as reductive iron or electrolytic iron and effecting the reaction at a temperature of 80° to 100° C.

Conversion of the nitrophenol (V) into the aminophenol (VII) may be accomplished by any per se conventional reduction procedure for changing a nitro group to an amino group. Examples of such reduction procedure are catalytic reduction, reduction with iron powder, reduction with sodium sulfide, reduction with sulfurated sodium borohydride, etc. For instance, treatment of one molar amount of the nitrophenol (V) with a 3 molar amount of hydrogen in the presence of a 1/10 to 1/100 molar amount of platinum dioxide in an inert solvent (e.g. ethanol, ethyl acetate) at room temperature under atmospheric pressure affords the aminophenol (VII). Further, for instance, treatment of one molar amount of the nitrophenol (V) with a 2 to 5 molar amount of iron powder such as reductive iron or electrolytic iron in a 5% acetic acid solution or a dilute hydrochloric acid solution at a temperature of 80° to 100° C. for a period of 1 to 5 hours produces the aminophenol (VII).

For production of the hydroxyphenyltetrahydrophthalimide (III) from the aminophenol (VII), the latter is reacted with 3,4,5,6-tetrahydrophthalic anhydride in an inert solvent (e.g. acetic acid) while refluxing for a period of 1 to 6 hours, preferably of 2 to 4 hours.

Still, the phenol (IV) is known (cf. Finger et al: J. Am. Chem. Soc., 81, 94 (1959)).

Practical and presently preferred embodiments of the production of the objective tetrahydrophthalimide (I) as well as the intermediary compounds including those of the formulas:

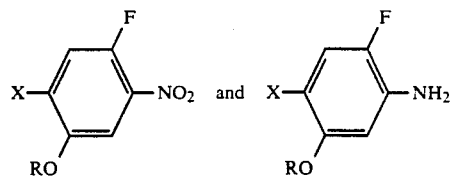

wherein R is a hydrogen atom or an isopropyl group and X is as defined above are illustratively shown below:

EXAMPLE 1

Production of the tetrahydrophthalimide (I: X=CL; R=iso—$C_3H_7$):

4-Chloro-2-fluoro-5-isopropoxyaniline (1.3 g) and 3,4,5,6-tetrahydrophthalic anhydride (1.12 g) were dissolved in acetic acid (10 ml) and refluxed for 3 hours. The resultant mixture was allowed to cool to room temperature and poured into water, followed by extraction with ether. The ether extract was washed with water, dried over anhydrous sodium sulfate and subjected to filtration. The filtrate was concentrated under reduced pressure and the residue was purified by silica gel chromatography to obtain 1.0 g of N-(4-chloro-2-fluoro-5-isopropoxyphenyl)-3,4,5,6-tetrahydrophthalimide (Compound No. 1). M.P., 81°–82° C.

NMR (CCl$_4$) δ (ppm): 1.35 (6H, d, J=6 Hz), 1.75 (4H, m), 2.3 (4H, m), 4.4 (1H, q, J=6 Hz), 6.65 (1H, d, J=6 Hz), 7.1 (1H, d, J=10 Hz):

EXAMPLE 2

Production of the tetrahydrophthalimide (I: X=Cl; R=iso—$C_3H_7$):

To a solution of N-(4-chloro-2-fluoro-5-hydroxyphenyl)-3,4,5,6-tetrahydrophthalimide (2.95 g) in dimethylformamide (20 ml), there was added anhydrous potassium carbonate (0.8 g) while stirring at room temperature. After stirring for 10 minutes at about 40° C., isopropyl iodide (1.7 g) was added thereto, and the resultant mixture was stirred for 3 hours at 70°–80° C. After being allowed to col to room temperature, the mixture was poured into water and extracted with toluene. The toluene layer was washed with water, dried over anhydrous sodium sulfate and concentrated. The residue was purified by silica gel chromatography to obtain 1.2 g of N-(4-chloro-2-fluoro-5-isopropoxyphenyl)3,4,5,6-tetrahydrophthalimide (Compound No. 1). M.P., 81°–82° C.

EXAMPLE 3

Production of the tetrahydrophthalimide (I: X=Br; R=iso—$C_3H_7$):

4-Bromo-2-fluoro-5-isopropoxyaniline (2.0 g) and 3,4,5,6-tetrahydrophthalic anhydride (1.23 g) were dissolved in acetic acid (10 ml) and refluxed for 3 hours. The resultant mixture was allowed to cool to room temperature and poured into water, followed by extraction with ether. The ether extract was washed with water, dried over anhydrous sodium sulfate and subjected to filtration. The filtrate was concentrated under reduced pressure, and the residue was purified by silica gel chromatography to obtain 1.6 g of N-(4-bromo-2-fluoro-5-isopropoxyphenyl)-3,4,5,6-tetrahydrophthalimide (Compound No. 2). M.P., 116.5°–117.5° C.

NMR (CDCl$_3$) δ (ppm): 1.35 (6H, d, J=6 Hz), 1.75 (4H, m), 2.3 (4H, m), 4.4 (1H, q, J=6 Hz), 6.75 (1H, d, J=6 Hz), 7.35 (1H, d, J=10 Hz).

EXAMPLE 4

Production of the aniline (II: X=Cl; R=iso—C$_3$H$_7$):

A suspension of 4-chloro-2-fluoro-5-isopropoxynitrobenzene (13.5 g) and platinum dioxide (0.4 g) in ethanol (300 ml) was subjected to catalytic reduction with hydrogen under room temperature and atmospheric pressure, whereby a designed amount of hydrogen was absorbed. The resultant mixture was filtered to remove insoluble materials, and the filtrate was concentrated. The residue was subjected to purification by silica gel chromatography to obtain 5.6 g of 4-chloro-2-fluoro-5-isopropoxyphenylaniline. $n_D^{24.5}$ 1.5360.

NMR (CDCl$_3$) δ (ppm): 1.3 (6H, d, J=6 Hz), 3.7 (2H, m, J=1.5 Hz), 4.35 (1H, q, J=7 Hz), 7.1 (1H, d, J=10 Hz).

IR $\nu_{max}$ (cm$^{-1}$): 3450, 3550.

In the same manner as above, there can be produced 4-bromo-2-fluoro-5-isopropoxyphenylaniline. $n_D^{25.0}$ 1.5547.

EXAMPLE 5

Production of the hydroxyphenyltetrahydrophthalimide (III: X=Cl):

2-Chloro-4-fluoro-5-aminophenol (6.6 g) and 3,4,5,6-tetrahydrophthalic anhydride (6 g) were dissolved in acetic acid (20 ml) and refluxed for 2 hours. The resultant mixture was allowed to cool to room temperature and poured into ice-water, followed by extraction with ether. The ether extract was washed with a saturated sodium hydrogen carbonate solution and water in this order, dried over anhydrous magnesium sulfate and concentrated. The residue was purified by silica gel chromatography to obtain 4.0 g of N-(4-chloro-2-fluoro-5-hydroxyphenyl)-3,4,5,6-tetrahydrophthalimide. M.P., 151° C.

NMR (CDCl$_3$, D$_6$-DMSO) δ (ppm): 1.5-2.0 (4H, m), 2.1-2.6 (4H, m), 6.8 (1H, d, J=6 Hz), 7.15 (1H, d, J=10 Hz).

IR $\nu_{max}^{nujol}$ (cm$^{-1}$): 3380, 1680.

EXAMPLE 6

Production of the hydroxyphenyltetrahydrophthalimide (III: X=Br):

In the same manner as in Example 5 but using 2-bromo-4-fluoro-5-aminophenol in place of 2-chloro-4-fluoro-5-aminophenol, there was produced N-(4-bromo-2-fluoro-5-hydroxyphenyl)-3,4,5,6-tetrahydrophthalimide. M.P., 167°-168° C.

NMR (CDCl$_3$, D$_6$-DMSO) δ (ppm): 1.5-2.0 (4H, m), 2.1-2.7 (4H, m), 6.8 (1H, d, J=6 Hz), 7.25 (1H, d, J=10 Hz).

IR $\nu_{max}^{nujol}$ (cm$^-$): 3380, 1690.

EXAMPLE 7

Production of the alkoxy-nitrobenzene (VI: X=Cl; R=iso—C$_3$H$_7$):

To a solution of 2-chloro-4-fluoro-5-nitrophenol (19.1 g) in acetonitrile (100 ml), there was added anhydrous potassium carbonate (8 g). After stirring at room temperature for several minutes, isopropyl iodide (25 g) was added thereto, and the resultant mixture was heated under reflux for 3 hours. After being allowed to cool to room temperature, water was added thereto, and the reaction mixture was extracted with ether. The ether extract was washed with a 5% aqueous sodium hydroxide solution and water in this order, dried over anhydrous magnesium sulfate and subjected to filtration. The filtrate was concentrated under reduced pressure, and the residue was recrystallized from ethanol to obtain 13.5 g of 4-chloro-2-fluoro-5-isopropoxynitrobenzene. M.P., 61.3°62.4° C.

NMR (CDCl$_3$) δ (ppm): 1.42 (6H, d, J=7 Hz), 4.3-4.8 (1H, m), 7.28 (1H, d, J=10 Hz), 7.48 (1H, d, J=6 Hz).

In the same manner as above, there can be produced 4-bromo-2-fluoro-5-isopropoxynitrobenzene. M.P., 65.5°-66.5° C.

EXAMPLE 8

Production of the aminophenol (VII: X=Cl):

A suspension of 2-chloro-4-fluoro-5-nitrophenol (9.17 g) and platinum dioxide (500 mg) in ethanol (120 ml) was subjected to catalytic reduction with hydrogen under room temperature and atmospheric pressure until a designed amount of hydrogen was absorbed. The catalyst was removed by filtration, and the filtrate was concentrated. The residue was extracted with ether, and the ether layer was concentrated to obtain 6.6 g of 3-amino-6-chloro-4-fluorophenol. M.P., 145°-146° C. (decomp.).

NMR (CDCL$_3$, D$_6$-DMSO) δ (ppm): 6.4 (1H, d, J=8 Hz), 6.85 (1H, d, J=11 Hz).

IR $\nu_{max}^{nujol}$ (cm$^{-1}$): 3400, 3320.

EXAMPLE 9

Production of the aminophenol (VII: X=Br):

In the same manner as above but using 2-bromo-4-fluoro-5-nitrophenol in place of 2-chloro-4-fluoro-5-nitrophenol, there was produced 3-amino-6-bromo-4-fluorophenol. M.P., 129°-130.5° C. (decomp.).

NMR (CDCl$_3$, D$_6$-DMSO) δ (ppm(): 6.57 (1H, d, J=8 Hz), 7.1 (1H, d, J=11 Hz).

IR $\nu_{max}^{nujol}$ (cm$^{-1}$): 3400, 3320.

EXAMPLE 10

Production of the nitrophenol (V: X=Cl):

2-Chloro-4-fluorophenol (83.4 g) was added to a solution of sodium hydroxide (27.7 g) in water (450 ml), and methyl chloroformate (69.2 g) was dropwise added thereto at a temperature of below 10° C. Precipitated crystals were collected by filtration and washed with water to give methyl (2-chloro-4-fluorophenyl)formate (134.8 g). M.P., 69°-71° C.

Methyl (2-chloro-4-Fluorophenyl) formate (134.8 g) obtained above was suspended in conc. sulfuric acid (50 ml). To the suspension, a mixture of conc. sulfuric acid (50 ml) and conc. nitric acid (50 ml) was added at about 30° C., and the mixture was stirred for 1 hour at this temperature. The reaction mixture was poured into ice-water, and precipitated crystals were collected and washed with water. Methyl (2-chloro-4-fluoro-5-nitrophenyl)formate (143 g) was thus obtained. M.P., 53°-55° C.

The product obtained as above was combined with sodium hydroxide (27 g) and water (300 ml), and the resultant mixture was refluxed for 4 hours. Precipitated insoluble materials were filtered using a celite, and the filtrate was acidified with conc. hydrochloric acid. Precipitated crystals were filtered and washed with water to obtain 76.3 g of 2-chloro-4-fluoro-5-nitrophenol. M.P. 106°-107° C.

NMR (CDCl$_3$, D$_6$-DMSO) δ (ppm): 7.25 (1H, d, J=10 Hz), 7.64 (1H, d, J=6 Hz).

IR $\nu_{max}^{nujol}$ (cm$^{-1}$): 3370.

EXAMPLE 11

Production of the nitrophenol (V: X=Br):

2-Bromo-4-fluorophenol (28 g) was added to a solution of sodium hydroxide (7 g) in water (100 ml), and methyl chloroformate was dropwise added thereto at a temperature of below 10° C. Precipitated crystals were collected by filtration and washed with water to give methyl (2-bromo-4-fluorophenyl)formate (41 g). M.P., 80.7° C.

The thus obtained methyl (2-bromo-4-fluorophenyl)formate was suspended in conc. sulfuric acid (13 ml). To the suspension, a mixture of conc. sulfuric acid (13 ml) and conc. nitric acid (13 ml) was added at about 30° C. The mixture was stirred for 30 minutes and poured into ice. Precipitated crystals were thoroughly washed with water, whereby yellow crystals of methyl (2-bromo-4-fluoro-5-nitrophenyl)formate (38.3 g) were obtained. M.P., 63.5°–64.5° C.

The product thus obtained was refluxed together with sodium hydroxide (6.2 g) and water (100 ml) for 3 hours. Insoluble materials were filtered, and the filtrate was acidified with hydrochloric acid. Precipitated crystals were collected by filtration and washed with water to obtain 25 g of 2-bromo-4-fluoro-5-nitrophenol. M.P., 126°–127° C.

NMR (CDCl$_3$, D$_6$-DMSO) δ (ppm): 7.42 (1H, d, J=10 Hz), 7.65 (1H, d, J=6 Hz).

IR $\nu_{max}^{nujol}$ (cm$^{-1}$): 3450.

In the practical usage of the tetrahydrophthalimides (I), they may be applied as such or in any preparation form such as wettable powders, emulsifiable concentrates, granules, suspensions or dusts.

In producing such a preparation form, a solid or liquid carrier may be used. As for the solid carrier, there may be exemplified mineral powders (e.g. kaolin, bentonite, montmorillonite, talc, diatomaceous earth, mica, vermiculite, gypsum, calcium carbonate, apatite, synthetic water-containing silicon hydroxide), vegetable powders (e.g. soybean powder, wheat flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethyleneoxypropylene polymers, polyoxyethylene alkyl phosphates, fatty acid salts, alkyl sulfates, alkyl sulfonates, alkylaryl sulfonates, alkyl phosphates, polyoxyethylene alkyl sulfate, quaternary ammonium salts, and the like. But the surface active agent is not of course limited to these compounds. And, if necessary, gelatin, casein, sodium alginate, starch, agar, polyvinyl alcohol, ligninsulfonic acid or the like may be used as an auxiliary agent.

In the preparation of a herbicidal composition, the content of the tetrahydrophthalimide (I) may be from 1 to 95% by weight, preferably from 3 to 80% by weight.

The tetrahydrophthalimide (I) of the invention may be used together with other herbicides to improve their activity as herbicides, and in some cases, a synergistic effect can be expected. Further, they may be also applied in combination with insecticides, nematocides, fungicides, plant growth regulators or fertilizers, depending upon the needs.

The dosage rate of the tetrahydrophthalimide (I) may vary on their kinds, the sorts of cultivated plants, the modes of application, etc. Generally, however, the dosage rate is from 0.1 to 50 grams, preferably from 0.5 to 30 grams, of the active ingredient per are.

Practical embodiments of the herbicidal composition according to the invention are illustratively shown in the following examples wherein parts and % are by wight.

Preparation Example 1

Eighty pats of Compound No. 1 or 2, 3 parts of alkylsulfate, 2 parts of ligninsulfonate and 15 parts of water-containing silicon hydroxide are well mixed while being powdered to obtain a wettable powder.

Preparation Example 2

Ten parts of Compound No. 1 or 2, 3 parts of alkylarylsulfate, 7 parts of polyoxyethylene alkylaryl ether, 60 parts of cyclohexanone and 20 parts of xylene are well mixed while being powdered to obtain an emulsifiable concentrate.

Preparation Example 3

Five parts of Compound No. 1 or 2, 1 part of water-containing silicon hydroxide, 35 parts of bentonite and 59 parts of kaolin are well mixed while being powdered. The mixture is then kneaded with water, granulated and dried to obtain a granule.

Preparation Example 4

Three parts of Compound No. 1 or 2, 0.3 part of isopropyl phosphate, 66.7 parts of kaolin and 30 parts of talc are well mixed while being powdered to obtain a dust.

Preparation Example 5

Twenty parts of Compound No. 1 or 2 is mixed with 60 parts of of an aqueous solution containing 3% polyoxyethylene sorbitan monolaurate and grained until the particle size of the active ingredient becomes less than 3 microns. Twenty parts of an aqueous solution containing 3% of sodium alginate as a dispersing agent is introduced therein to obtain a suspension.

The application of the tetrahydrophthalimides (I) as herbicides will be illustratively shown in the following Examples wherein the phytotoxicity to cultivated plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and control weeds, respectively. The rating values in the paddy field test along were calculated from the dry weight of the test plants.

| Rating value | Fresh weight (percentage to untreated plot) (%) | |
|---|---|---|
| | Crop plant | Weeds |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples:

| Examples: Compound No. | Structure | Remarks |
|---|---|---|
| A | (2-fluoro-4-chlorophenyl tetrahydrophthalimide structure) | U.S. Pat. No. 4,032,326 |
| B | (2,4-dichloro-5-isopropoxyphenyl tetrahydrophthalimide structure) | U.K. Patent Publn. No. 2046754A |
| C | $(CH_3)_2CHNH-$ triazine $-Cl$, $HNCH_2CH_3$ | Atrazine |

Test Example 1

Plastic trays (35 cm × 25 cm × 10 cm) were filled with upland field soil, and the seeds of corn, velvetleaf, sunflower, sicklepod, tall morningglory, wild mustard and common chickweed were separately sowed in the trays and grown for 2 weeks in the greenhouse. Each of two trays was set in a frame (50 cm × 100 cm × 40 cm) and a designed amount of the test compound was sprayed to the foliage of the test plants over the top by means of a small hand sprayer. After the spraying, the test plants were further grown for 3 weeks in the greenhouse, and herbicidal activity and phytotoxicity were examined. The results are shown in Table 1. In this foliar treatment, the test compounds were formulated into an emulsifiable concentrate according to Preparation Example 2 and applied by dispersing it in 25 ml of water with the addition of a spreading agent. At the time of application, the test plants were in a 1 to 3-leaf stage and 2 to 20 cm in height.

TABLE 1

| Compound No. | Dosage (weight of active ingredient, g/are) | Phytotoxicity Corn | Herbicidal activity | | | | | |
|---|---|---|---|---|---|---|---|---|
| | | | Velvetleaf | Sunflower | Sicklepod | Tall morningglory | Wild mustard | Common chickweed |
| 1 | 2.5 | 1 | 5 | 5 | 5 | 5 | 5 | 5 |
| | 1.25 | 1 | 5 | 5 | 5 | 5 | 5 | 4 |
| | 0.63 | 0 | 5 | 5 | 4 | 5 | 4 | 3 |
| 2 | 2.5 | 1 | 5 | 5 | 5 | 5 | 5 | 5 |
| | 1.25 | 1 | 5 | 5 | 5 | 5 | 5 | 4 |
| | 0.63 | 0 | 5 | 4 | 3 | 5 | 4 | 3 |
| A | 10 | 3 | 5 | 5 | 4 | 5 | 5 | 2 |
| | 5 | 3 | 5 | 5 | 4 | 5 | 4 | 1 |
| | 2.5 | 2 | 5 | 4 | 3 | 4 | 3 | 1 |
| | 1.25 | 1 | 3 | 2 | 1 | 3 | 2 | 0 |
| B | 10 | 3 | 5 | 5 | 4 | 5 | 5 | 3 |
| | 5 | 2 | 5 | 5 | 3 | 4 | 4 | 2 |
| | 2.5 | 2 | 4 | 4 | 2 | 4 | 3 | 1 |
| | 1.25 | 0 | 2 | 3 | 0 | 2 | 1 | 0 |
| C | 10 | 0 | 5 | 5 | 2 | 5 | 5 | 5 |
| | 5 | 0 | 3 | 5 | 0 | 4 | 5 | 5 |

Test Example 2

Seeds of corn and broad-leaved weeds such as cocklebur, common purslane and tall morningglory were sowed in the field as previously laid up in ridges, each ridge having an upper width of 1 m. At the time when the corn grew up to the 6-leaf stage and the broad-leaved weeds up to 2 to 5-leaf stages, a designed amount of the test compound formulated into an emulsifiable concentrate according to Preparation Example 2 and dispersed in water was sprayed to the foliage of the test plants with three replications over the top by means of a small hand sprayer at a spray volume of 5 liters per are. After cultivation for 3 weeks, herbicidal activity and phytotoxicity were examined. The results are shown in Table 2.

TABLE 2

| Compound No. | Dosage (weight of active ingredient, g/are) | Phytotoxicity Corn | Herbicidal activity | | |
|---|---|---|---|---|---|
| | | | Cocklebur | Common purslane | Tall morningglory |
| 1 | 0.63 | 1 | 5 | 5 | 5 |
| | 0.32 | 1 | 5 | 5 | 4 |
| | 0.16 | 0 | 5 | 5 | 3 |
| A | 1.25 | 1 | 4 | 3 | 2 |
| | 0.63 | 0 | 1 | 2 | 2 |
| B | 1.25 | 1 | 4 | 4 | 4 |

TABLE 2-continued

| Compound No. | Dosage (weight of active ingredient, g/are) | Phytotoxicity Corn | Herbicidal activity | | |
|---|---|---|---|---|---|
| | | | Cocklebur | Common purslane | Tall morning-glory |
| | 0.63 | 1 | 2 | 3 | 3 |

Test Example 3

Seeds of corn, tall morningglory, velvetleaf, jimsonweed, common ragweed, ladysthumb, redroot pigweed and green foxtail were sowed in the field as previously laid up in ridges, each ridge having an upper width of 1 m. Thereafter, the ridges were plotted in 3 m² and a designed amount of the test compound formulated into an emulsifiable concentrate according to Preparation Example 2 was dispersed in water and applied by spraying to the plots with three replications over the top by means of a small hand sprayer at a spray volume of 5 liters per are. After cultivation for 5 weeks, herbicidal activity and phytotoxicity were examined. The results are shown in Table 3.

TABLE 3

| Compound No. | Dosage (weight of active ingredient, g/are) | Phytotoxicity Corn | Herbicidal activity | | | | | | | |
|---|---|---|---|---|---|---|---|---|---|---|
| | | | Cocklebur | Tall morning-glory | Velvetleaf | Jimsonweed | Common ragweed | Ladysthumb | Redroot pigweed | Green foxtail |
| 1 | 8 | 0 | 5 | 5 | 5 | 5 | 5 | 5 | 5 | 5 |
| | 4 | 0 | 4 | 5 | 5 | 5 | 5 | 5 | 5 | 4 |
| C | 20 | 0 | 0 | 3 | 2 | 5 | 4 | 5 | 5 | 0 |
| | 10 | 0 | 0 | 2 | 1 | 3 | 2 | 4 | 3 | 0 |

Test Example 4

Wagner's pots (1/5000 are) were filled with paddy field soil containing the seeds of broad-leaved weeds (e.g. monochoria, false pimpernel, toothcup) and the seeds of barnyardgrass and hardstem bulrush, and water was poured therein until the depth of water became 4 cm. Rice seedlings of the 3.5-leaf stage and the tubers of arrowhead were transplanted therein and grown for 2 days in a greenhouse. A designed amount of the test compound formulated in an emulsifiable concentrate according to Preparation Example 2 was applied to the pots by perfusion. Thereafter, the test plants were grown for an additional 3 weeks in the greenhouse, and herbicidal activity and phytotoxicity were examined. The results are shown in Table 4. In this treatment, the emulsifiable concentrate was dispersed in water for application at a perfusion volume of 10 liters per are.

The invention being thus described, it will be obvious that the same may be varied in many ways. Such variations are not to be regarded as a departure from the spirit and scope of the invention.

TABLE 4

| Compound No. | Dosage (weight of active ingredient, g/are) | Phytotoxicity Rice plant | Herbicidal activity | | | |
|---|---|---|---|---|---|---|
| | | | Barnyardgrass | Broad-leaved weed | Hardstem bulrush | Arrowhead |
| 1 | 2.5 | 1 | 5 | 5 | 5 | 5 |
| | 1.25 | 0 | 5 | 5 | 4 | 4 |
| 2 | 2.5 | 1 | 5 | 5 | 5 | 5 |
| | 1.25 | 0 | 4 | 5 | 4 | 4 |
| A | 2.5 | 1 | 2 | 5 | 3 | 0 |
| | 1.25 | 0 | 1 | 5 | 2 | 0 |
| B | 2.5 | 0 | 3 | 5 | 2 | 0 |
| | 1.25 | 0 | 1 | 5 | 1 | 0 |

What is claimed is:

1. A compound of the formula:

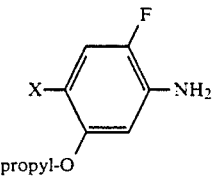

wherein X is a chlorine atom or a bromine atom.

2. A compound of the formula:

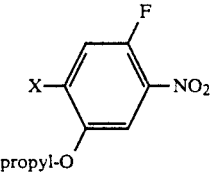

wherein x is a chlorine atom or a bromine atom.

3. A compound as in claim 1, wherein X is chlorine.
4. A compound as in claim 1, wherein X is bromine.
5. A compound as in claim 2, wherein X is chlorine.
6. A compound as in claim 2, wherein X is bromine.

UNITED STATES PATENT AND TRADEMARK OFFICE
CERTIFICATE OF CORRECTION

PATENT NO. : 5,030,761
DATED : July 9, 1991
INVENTOR(S) : Eiki Nagano et al.

It is certified that error appears in the above-identified patent and that said Letters Patent is hereby corrected as shown below:

On the title page, in Item [54] and in column 1, lines 1-5, change "TETRAHYDROPHTALIMIDES" to --TETRAHYDROPHTHALIMIDES--; and in Item "[21] Appl. No.:" change "553,391" to --553,991--.

Signed and Sealed this

Fifth Day of January, 1993

Attest:

DOUGLAS B. COMER

Attesting Officer

Acting Commissioner of Patents and Trademarks